(12) United States Patent
Onishi et al.

(10) Patent No.: US 12,029,670 B2
(45) Date of Patent: Jul. 9, 2024

(54) STENT DELIVERY DEVICE

(71) Applicant: OLYMPUS CORPORATION, Tokyo (JP)

(72) Inventors: Taihei Onishi, Yokohama (JP); Toshihiro Yamagata, Hachioji (JP); Hirofumi Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 170 days.

(21) Appl. No.: 17/552,243

(22) Filed: Dec. 15, 2021

(65) Prior Publication Data

US 2022/0192852 A1 Jun. 23, 2022

Related U.S. Application Data

(60) Provisional application No. 63/129,996, filed on Dec. 23, 2020.

(51) Int. Cl.
*A61F 2/966* (2013.01)
*A61F 2/90* (2013.01)
*A61F 2/95* (2013.01)

(52) U.S. Cl.
CPC ............ *A61F 2/966* (2013.01); *A61F 2/90* (2013.01); *A61F 2002/9505* (2013.01); *A61F 2002/9528* (2013.01); *A61F 2002/9665* (2013.01)

(58) Field of Classification Search
CPC .... A61F 2/966; A61F 2/90; A61F 2002/9505; A61F 2002/9528; A61F 2002/9666;
(Continued)

(56) References Cited

U.S. PATENT DOCUMENTS 5,954,729 A * 9/1999 Bachmann ............. A61B 17/29
606/198
7,473,271 B2 1/2009 Gunderson
(Continued)

FOREIGN PATENT DOCUMENTS

JP 2003-500104 A 1/2003
JP 2006-522654 A 10/2006
(Continued)

OTHER PUBLICATIONS

Office Action dated Nov. 8, 2022, issued in corresponding Japanese Patent Application No. 2021-206118.

*Primary Examiner* — Kathleen S Holwerda
*Assistant Examiner* — Daniel Icet
(74) *Attorney, Agent, or Firm* — Morgan, Lewis & Bockius LLP

(57) ABSTRACT

A stent delivery device for delivering a self-expanding stent comprises an inner sheath including a proximal end portion and a distal end portion, a stent stopper including a stopper main body that is circumferentially disposed over at least a portion of the inner sheath at the proximal end portion, and at least one projection extending radially outward from the stopper main body for releasably engaging a portion of the self-expanding stent, and an outer sheath slidably disposed over the inner sheath and the stent stopper. The at least one projection includes a distal end surface and a proximal end surface, and the proximal end surface includes a recess extending into a body of the projection toward the distal end surface.

22 Claims, 13 Drawing Sheets

(58) Field of Classification Search
CPC .... A61F 2002/9534; A61F 2/95; A61F 2/962; A61F 2/2427; A61F 2/97
See application file for complete search history.

(56) References Cited

U.S. PATENT DOCUMENTS

| | | | | |
|---|---|---|---|---|
| 8,337,543 B2* | 12/2012 | Jordan | ................... | A61F 2/966 623/1.53 |
| 9,220,620 B2* | 12/2015 | Hadley | ................... | A61F 2/966 |
| 2004/0204749 A1 | 10/2004 | Gunderson | | |
| 2004/0267348 A1 | 12/2004 | Gunderson et al. | | |
| 2008/0009934 A1 | 1/2008 | Schneider et al. | | |
| 2011/0029065 A1 | 2/2011 | Wood et al. | | |
| 2012/0150272 A1* | 6/2012 | Melsheimer | ............ | A61F 2/966 623/1.11 |
| 2014/0135907 A1* | 5/2014 | Gallagher | ................ | A61F 2/95 623/2.11 |
| 2016/0143761 A1 | 5/2016 | Wood et al. | | |
| 2017/0079819 A1 | 3/2017 | Pung et al. | | |
| 2019/0142617 A1 | 5/2019 | Pung et al. | | |
| 2019/0216626 A1 | 7/2019 | Wood et al. | | |
| 2019/0282384 A1 | 9/2019 | Phillips | | |

FOREIGN PATENT DOCUMENTS

| | | | |
|---|---|---|---|
| JP | 2006-522668 | A | 10/2006 |
| JP | 2009-542357 | A | 12/2009 |
| JP | 4754479 | B2 | 8/2011 |
| JP | 4796488 | B2 | 10/2011 |
| JP | 2013-500777 | A | 1/2013 |
| JP | 5716025 | B2 | 5/2015 |
| JP | 2018-531664 | A | 11/2018 |
| JP | 6816126 | B2 | 1/2021 |
| WO | 00/71058 | A1 | 11/2000 |
| WO | 2004/091446 | A2 | 10/2004 |

* cited by examiner

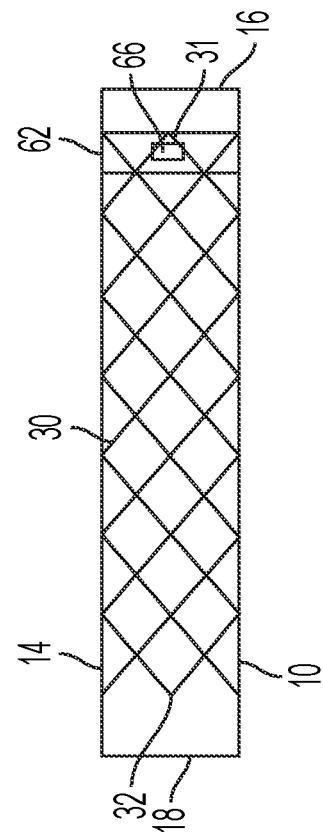
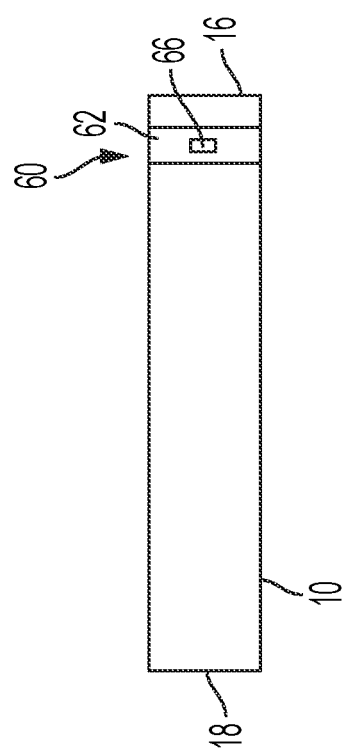
FIG. 2B
FIG. 2A

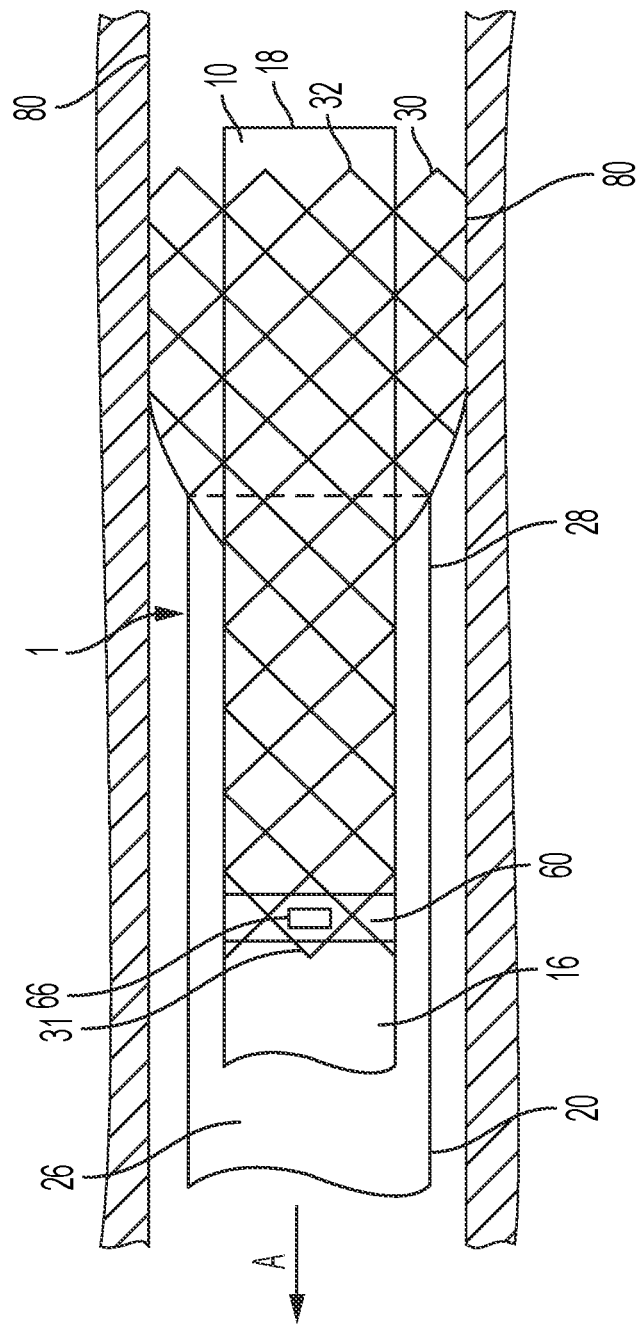

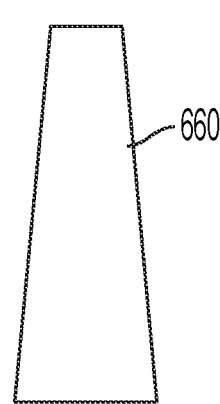
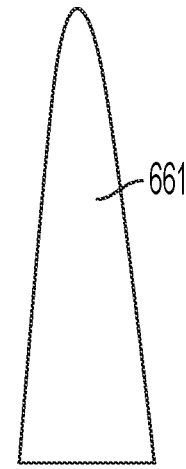
FIG. 6A    FIG. 6B
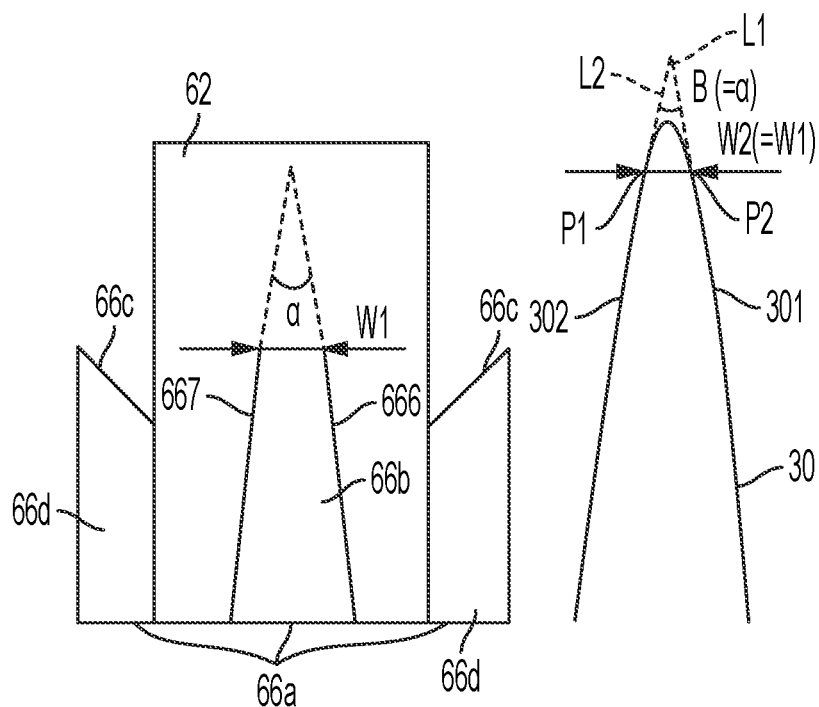
FIG. 7

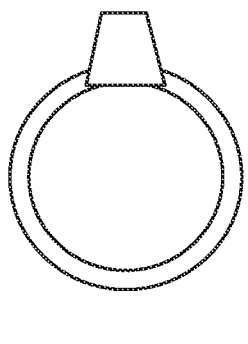
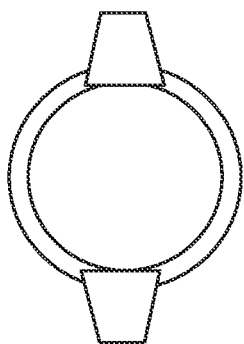
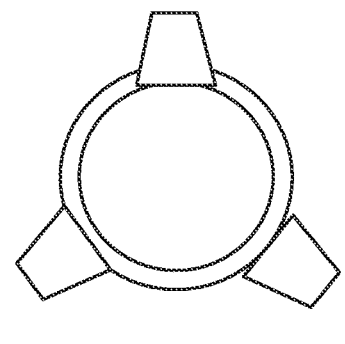
FIG. 13A  FIG. 13B  FIG. 13C
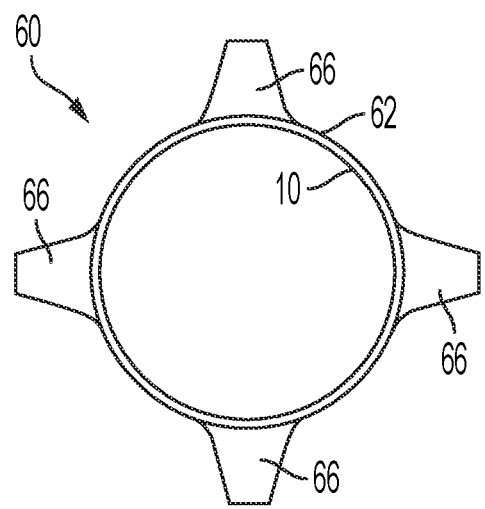
FIG. 13D

STENT DELIVERY DEVICE

RELATED APPLICATION DATA

This application is based on and claims priority under 35 U.S.C. § 119 to U.S. Provisional Application No. 63/129,996, filed Dec. 23, 2020, the entire contents of which are incorporated herein by reference.

FIELD OF THE INVENTION

The present invention relates to a stent delivery device and system, and more particularly, to a stent delivery device and system in which a stent stopper is disposed on an inner sheath for releasing and/or recapturing a self-expandable stent.

DESCRIPTION OF THE RELATED ART

In medicine, stents are metal or plastic tubes inserted into the lumen of an anatomic vessel or duct to keep the passageway open, and stenting is an operation of placing a stent on a target area. Typically, a stent will have an unexpanded (reduced or closed) diameter for placement and an expanded (opened) diameter after placement in the vessel or the duct. Some stents are self-expanding, some stents are expanded mechanically with radial outward force from within the stent, as by inflation of a balloon; and some stents, known as hybrid stents, have one or more characteristics common to both self-expanding and mechanically expandable stents.

A self-expanded stent is usually delivered via an inner sheath in the unexpanded diameter state and covered by an outer sheath to a desired bodily location. Once at the desired bodily location, the outer sheath is pulled back to expose the stent so that the stent can be expanded and implanted in the bodily lumen.

In conventional stent delivery devices, particularly those used to deliver a self-expanding stent, the stent is typically retained on the inner sheath via the outer sheath as a retention device. The stent may be deployed by retracting the outer sheath from over the stent. To prevent the stent from being drawn longitudinally with the retracting outer sheath, many delivery systems provide the inner sheath shaft with one or more stent stoppers, such as bumpers, hubs, or the like.

However, it is known that in many cases, when the outer sheath is withdrawn from a stent, particularly, a self-expanding stent constructed of shape memory material, the stent may be displaced longitudinally relative to the inner sheath shaft because the stent tends to migrate or jump longitudinally relative to the stent mounting region of the inner sheath resulting in the imprecise delivery of the stent and/or distortion of the stent body. Therefore, when a surgeon feels that the stent is likely to miss a desired delivery bodily location during placement, a recapturing operation is performed in which the stent once deployed is re-contracted and re-stored in the delivery system for position adjustment. The stent stopper is typically used to perform the recapturing operation.

The stent stopper in a stent delivery device and system should be configured to restrain the stent on the inner sheath during recapture, and also not to hinder the behavior of the stent releasing from the delivery device by self-expansion when the stent is fully deployed. The conventional stent delivery device and systems have disadvantages in combining the two conflicting functions. Thus, it would be desirable to provide a stent delivery device and system, in which the stent stopper can effectively combine the conflicting functions of restraining and releasing a self-expanding stent.

SUMMARY OF THE INVENTION

Accordingly, the present disclosure is directed to a stent delivery device and system, which substantially obviate one or more of the issues due to limitations and disadvantages of related stent delivery device and system.

An object of the present disclosure is to provide a stent delivery device for delivering a self-expanding stent. The device comprises an inner sheath including a proximal end portion and a distal end portion, a stent stopper including a stopper main body that is circumferentially disposed over at least a portion of the inner sheath at the proximal end portion, and at least one projection extending radially outward from the stopper main body for releasably engaging a portion of the self-expanding stent, and an outer sheath slidably disposed over the inner sheath and the stent stopper. The at least one projection includes a distal end surface and a proximal end surface, and the proximal end surface includes a recess extending into a body of the projection toward the distal end surface.

Another object of the present disclosure is to provide a stent delivery device for delivering a self-expanding stent comprising an inner sheath including a proximal end portion and a distal end portion, a stent stopper including a stopper main body that is circumferentially disposed over at least a portion of the inner sheath at the proximal end portion, and at least one projection extending radially outward from the stopper main body for releasably engaging a portion of the self-expanding stent, and an outer sheath slidably disposed over the inner sheath and the stent stopper. The at least one projection includes a distal end surface, a proximal end surface, and an upper surface that is formed between the distal end surface and the proximal end surface. The upper surface is configured to have a substantially trapezoidal shape that narrows toward the proximal end surface in a longitudinal direction of the inner sheath.

Additional features and advantages will be set forth in the description that follows, and in part will be apparent from the description, or may be learned by practice of the invention. The objectives and other advantages of the disclosed stent delivery device and system will be realized and attained by the structure particularly pointed out in the written description and claims thereof as well as the appended drawings.

BRIEF DESCRIPTION OF THE DRAWING

The following detailed description of preferred embodiments can be read in connection with the accompanying drawings in which like numerals designate like elements and in which:

FIG. 2A is a planar view of a stent delivery device having an inner sheath and a stent stopper disposed on the inner sheath, and FIG. 2B a planar view of a stent delivery device having a stent disposed over the inner sheath of FIG. 2A according to one exemplary embodiment.

FIG. 3 is a planar view illustrating a stent delivery device that partially deploys a stent within a body lumen according to one embodiment of the invention.

FIG. 6A-6B are planar top views schematically illustrating the exemplary configurations of an upper surface of a projection of the stent stopper according to one exemplary embodiment.

FIG. 7 is another schematic view illustrating the structural configuration of the upper surface of the stent stopper of FIG. 6A according to one exemplary embodiment.

FIGS. 13A-13D are examples of the stent stopper according to additional embodiments.

DETAILED DESCRIPTION

Hereinafter, various exemplary embodiments of a stent delivery device and system according to the present invention will be described with reference to the drawings. Throughout all of the drawings, ratios of the thicknesses or dimensions of respective constituent elements are appropriately adjusted for clarity.

Figure 1A:
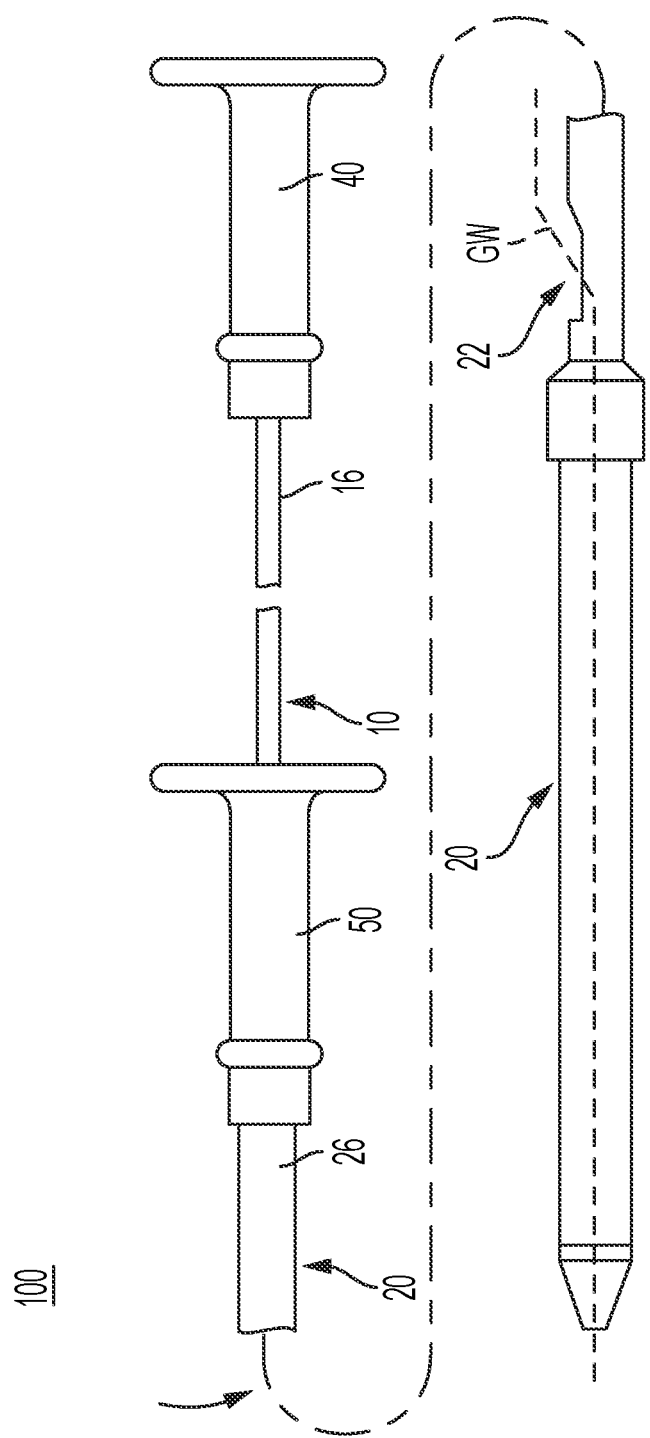
FIG. 1A is a planar view schematically showing a stent delivery system.
Figure 1B:
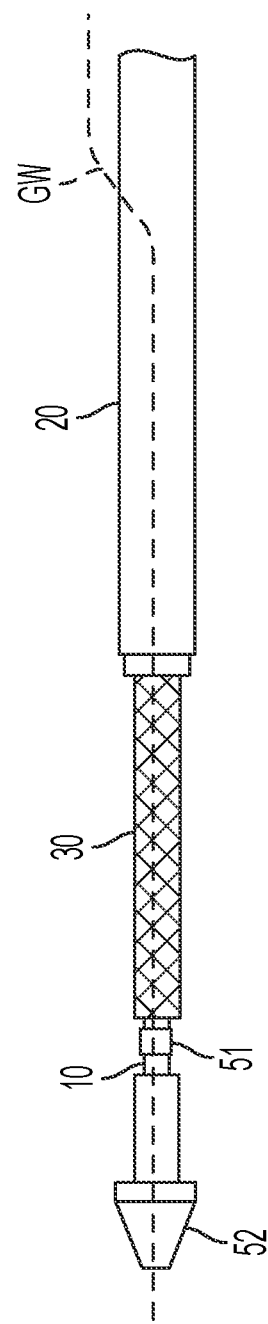
FIG. 1B is a planar view of a distal end portion of the stent delivery system of FIG. 1A according to one exemplary embodiment.

FIG. 1A is a planar view schematically showing a stent delivery system 100 according to an exemplary embodiment, and FIG. 1B is a planar view of a distal end portion of the stent delivery system of FIG. 1A.

As shown in FIG. 1A, the stent delivery system 100 is suitable for intraluminal applications, including, but not limited to, biliary applications and intravascular applications. In biliary applications, the stent delivery system 100 may be sized to fit within an endoscope (not shown) and to navigate to the desired site in the biliary tract. In vascular applications, the stent delivery system 100 may be sized to fit within an introducer sheath (not shown) and/or a guide catheter (not shown) to navigate to the desired vascular site.

The stent delivery system 100 includes an inner sheath 10 slidably disposed in an outer sheath 20. The outer sheath 20 includes a lumen (not visible) extending therethrough to slidably accommodate the inner sheath 10. The inner sheath 10 includes a guidewire lumen extending through a distal end portion thereof to accommodate a guidewire GW. The guidewire GW may exit through a guidewire opening 22 in the outer sheath 20.

The stent delivery system 100 is advanced over the guidewire GW to deliver and deploy a self-expanding stent 30 in a bodily lumen. The guidewire GW may be any guidewire as is known in the art. The guidewire GW is typically an elongated, relatively rigid, but typically flexible, cylindrical member. The guidewire GW may be constructed of any material, but is preferably constructed of metal, such as stainless steel, gold, platinum, and metal alloys such as cobalt-based alloys or titanium alloys, for example, nickel-titanium shape memory alloys (i.e., nitinol), titanium-aluminum-vanadium alloys and titanium-zirconium-niobium alloys. Moreover, the guidewire GW may have a constant stiffness or flexibility along the entire length thereof, or may have portions of varying stiffness and flexibility, such as an area of increased flexibility at the tip of the guidewire.

The guidewire GW may further include a coating along a portion or the entire length thereof, such as a lubricious or frictionless coating material. The guidewire may further be provided with a radiopaque portion, for example in the form of a radiopaque coating on a portion of the guidewire, or by constructing a portion of the guidewire out of a radiopaque material.

As illustrated by FIG. 1A, the stent delivery system 100 also includes a proximal handle 40 that is connected to a proximal end portion 16 of the inner sheath 10, and a distal handle 50 that is connected to a proximal end portion 26 of the outer sheath 20. The distal handle 50 may be longitudinally displaced relative to the proximal handle 40 to selectively expose or cover the stent 30. Referring to FIG. 1A, the distal handle 50 has been longitudinally displaced in the distal direction relative to the proximal handle 40 such that the outer sheath 20 covers the stent 30. Referring to FIG. 1B, the distal handle 50 has been longitudinally displaced relative to the proximal handle 40 to retract the outer sheath 20 relative to the inner sheath 10 to expose and deploy the stent 30.

A distal head 52 may be connected to the distal end of the distal inner portion of the inner sheath 10 to limit, if desired, distal displacement of the outer sheath 20. Radiopaque marker bands, for example marker 51, may be on the inner sheath 10 to facilitate placement of the stent 30 during intraluminal delivery.

The marker 51 may include any useful radiopaque material or materials including any metal or plastics being radiopaque or capable of being impregnated with radiopaque materials. Useful radiopaque materials include, but are not limited to gold, barium sulfate, ferritic particles, platinum, platinum-tungsten, palladium, platinum-iridium, rhodium, tantalum or combinations thereof.

The stent 30 may be made from any suitable implantable material, including without limitation nitinol, stainless steel, cobalt-based alloy such as Elgiloy, platinum, gold, titanium, tantalum, niobium, polymeric materials and combinations thereof Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly (glycolide-co-trimethylene carbonate) (PGAIPTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGAIPCL), poly(phosphate ester) and the like.

Further, the stent 30, or portions of the stent 30, may have a composite construction. For example, the stent 30 may have an inner core of tantalum gold, platinum, iridium or combination of thereof and an outer member or layer of nitinol to provide a composite wire for improved radiocapicity or visibility. Or the stent 30 may be made from nitinol.

Also, the stent 30 may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hiradin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anticoagulants (such as D-Phe-Pro-Arg chloromethyl keton, an ROD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors twin as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

The stent 30 may be coated with a polymeric material. For example, the stent wires of the stent 30 may be partially or fully covered with a biologically active material which is equitably disposed with the polymeric material. Further, the polymeric coating may extend over or through the interstitial spaces between the stent wires so as to provide a hollow tubular liner or cover over the interior or the exterior surface of the stent, thereby providing a stent-graft device. The polymeric material may be selected from the group consisting of polyester, polypropylene, polyethylene, polyurethane, polynaphthalene, polytetrafluoroethylene, expanded polytetrafluoroethylene, silicone, and combinations thereof. The covering may be in the form of a tubular structure. The silicone covering may be suitably formed by dip coating the stent. The present invention is not limited to forming the silicone film by dip coating, and other techniques, such as spraying, may suitably be used. After applying the silicone coating or film to the stent, the silicone may be cured. The curing may be low temperature curing, for example from about room temperature to about 90° C. for a short period of time, for example from about 10 minutes or more to about 16 hours. The cured silicone covering may also be sterilized by electronic beam radiation, gamma radiation ethylene oxide treatment and the like. Argon plasma treatment of the cured silicone may also be used. Argon plasma treatment of the cured silicone modifies the surface to the cured silicone to, among other things, make the surface less sticky. The invention, however, is not limited to stent-graft devices having polymeric coatings. The graft portion may suitably be formed from polymeric films, polymeric tapes, polymeric tubes, polymeric sheets and textile materials. Textile material may be woven, knitted, braided and/or filament wound to provide a suitable graft.

Various biocompatible polymeric materials may be used as textile materials to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. Moreover, textile materials and stent materials may be co-formed, for example co-braided, to form a stent-graft device.

Various self-expending stents may be employed in the invention. The self-expanding stents may include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents, including biodegradable and bio-absorbable stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

The stent delivery system 100 utilizes a stent delivery device 1, which includes the inner sheath 10, the outer sheath 20, and a stent stopper 60. As described above, the inner sheath 10 and the outer sheath 20 may be hollow tubes. The inner sheath 10 is disposed inside the outer sheath 20 such that they are slidably disposed relative to each other. In other words, the outer sheath 20 may be slid over the inner sheath 10, and/or the inner sheath 10 may be slid within the outer sheath 20.

The inner sheath 10 includes a proximal end 16 and an opposed distal end 18. The outer sheath 20 includes a proximal end 26 and a distal end 28. It should be noted that references herein to the term "distal" are to a direction away from the proximal handle 40, while references to the term "proximal" are to a direction towards the proximal handle 40.

The inner sheath 10 and/or the outer sheath 20 may be constructed of any suitable biocompatible materials, such as, but not limited to, polymeric polymers and materials, including fillers such as metals, carbon fibers, glass fibers or ceramics, and combinations thereof. Useful, but non-limiting, polymeric materials include polyethylene, polypropylene, polyvinyl chloride, polytetrafluoroethylene, fluorinated ethylene propylene copolymer, polyvinyl acetate, polystyrene, polyethylene terephthalate), naphthalene dicarboxylate derivatives, such as polyethylene naphthalate, polybutylene naphthalate, polytrimethyiene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, fully or partially halogenated polyethers, polyamidelpolyether polyesters, and copolymers and combinations thereof.

Further, the inner sheath 10 and/or the outer sheath 20 may be reinforced to provide greater strength while minimizing overall tube profile. For example, the inner sheath 10 and/or the outer sheath 20 may have a reinforcing material, for example a polymeric, metallic or ceramic strand or tape, encased within the tube or otherwise disposed on or within the tube. The reinforcing strand or tape may be braided, woven, wound, and the life to form a reinforcing member for the tube.

As shown in FIG. 2A, the stent stopper 60 of the stent delivery device 1 includes a stopper main body 62, which may be disposed at or near the proximal end 16 of the inner sheath 10. The stent stopper 60 also includes at least one projection 66, which is attached to or protrudes from the stopper main body 62. The projection 66 is configured to hold or secure the stent 30 during operation of the stent delivery device 1.

As shown in FIG. 2B, the stent 30 is disposed over the outer surface 14 of the inner sheath 10. The stent 30 is a hollow tubular device with an open lattice wall structure having a proximal end 31 and an opposed distal end 32. As illustrated in FIG. 2B, the projection 66 of the stent stopper 60 securably holds or retains one rhombus mesh of the proximal end 31 of the stent 30.

FIG. 3 is a planar depiction of partial deployment of the stent 30 within a body lumen according to one embodiment of the invention.

As illustrated in FIG. 3, the stent delivery device 1 partially deploys the stent 30 according to an exemplary embodiment. Specifically, after the stent delivery device 1 is placed within a body lumen 80, the outer sheath 20 may be retracted or slid away from the inner sheath 10. As the outer sheath 20 retracts in a direction of "A", the exposed distal end portion 32 of the stent 30 expands against the walls of the body lumen 80.

When the distal end 28 of the outer sheath 20 is retracted past the proximal end portion 16 of the inner sheath 10 having the stent stopper 60 disposed thereon, the stent 30 may be fully deployed with the body lumen 80. The stent delivery device 1 may be retracted from the body lumen 80, leaving the deployed stent 30 within the body lumen 80. Prior to full deployment of the stent 30, i.e., prior to retraction of the distal potion 28 of the outer sheath 20 past the stent stopper 60 disposed on the proximal end 16 of the inner sheath 10, the stent 30 may be repositioned within the body lumen 80. The outer sheath 20 may be repositioned over the inner sheath 10, such as by sliding, to recapture the stent 30 therebetween. The stent delivery device 1 may then be repositioned within the body lumen 80, followed by redeployment of the stent 30.

Figure 4:
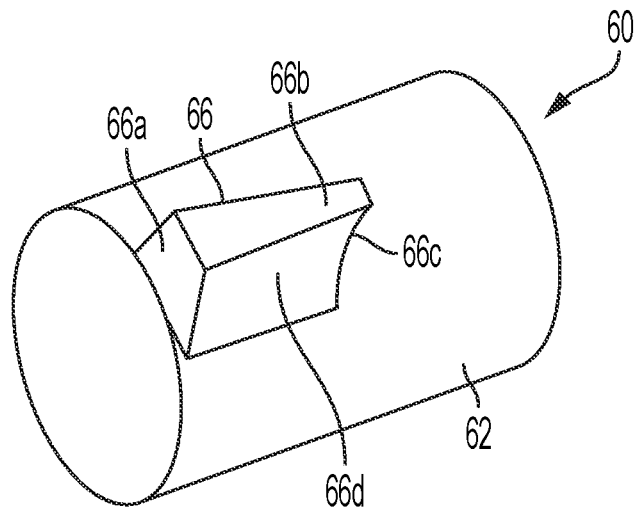
FIG. 4 is a perspective schematic view of a stent stopper of the stent delivery device of FIG. 3 according to one exemplary embodiment.
Figure 5:
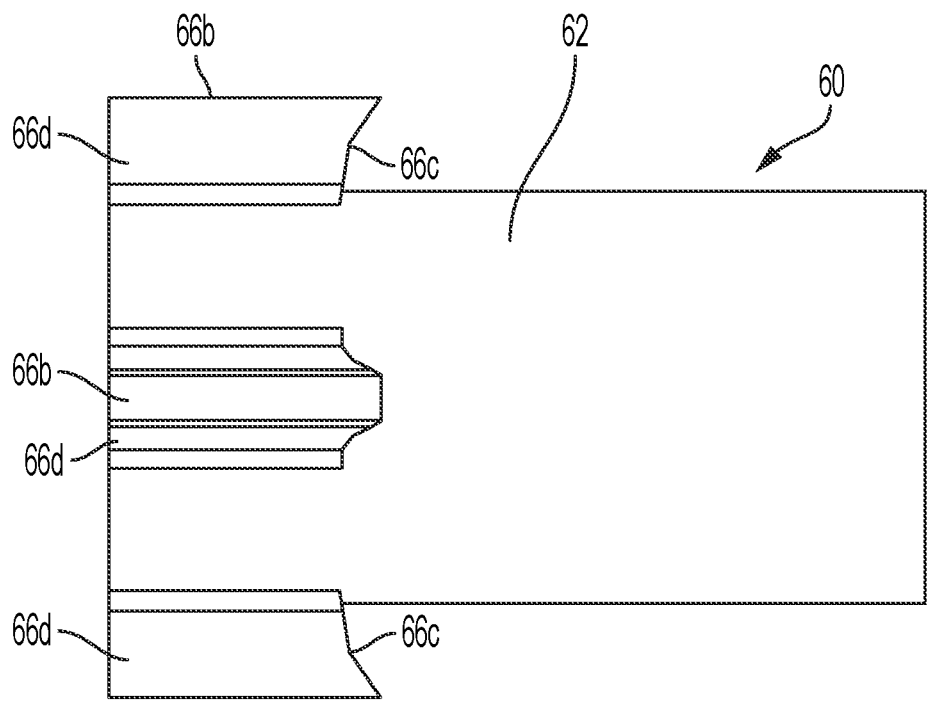
FIG. 5 is side view of a stent stopper according to one exemplary embodiment.

FIG. 4 is a perspective view of the stent stopper 60 according to one exemplary embodiment. The stent stopper 60 in FIG. 4 is enlarged for explanation purpose. FIG. 5 is a side view of a stent stopper according to one exemplary embodiment. As shown in FIG. 4, the stent stopper 60 may include the circumferential stopper main body 62 from which the projection 66 outwardly extends in a radial direction.

As shown in FIG. 4, the stent stopper 60 is a hollow tubular device. For explanation purpose, FIG. 4 only illustrates one projection 66 on the stent stopper 60. However, the stent stopper 60 of the invention is not limited to only one projection 66 attached to the stopper main body 62. As will be described later, the stent stopper 60 may include a pair of opposed projections 66, such that the projections 66 may be opposed from each other or in other words are disposed at about 180 degree from one and the other. The stent stopper 60 may also include more than two projections 66, which may be arranged in a regular or irregular interval surrounding the stopper main body 62.

The projection 66 may be a low-profile projection. Useful low-profile projections include, but are not limited to, round projections, convex projections, semicircular projections, lobate-shaped projections, fin-shaped projections and the like.

In the exemplary embodiment shown in FIG. 4, the projection 66 of the stent stopper 60 extends radially outward from the stopper main body 62 and includes a distal end surface 66a, an upper surface 66b, a proximal end surface 66c, and two side surfaces 66d. The projection 66 may have a bottom surface 66e (in FIG. 9A) that is attached to the stopper main body 62. Alternatively, the bottom surface 66e of the projection 66 may be integrally formed with the stopper main body 62.

The distal end surface 66a of the projection 66 is configured to have a substantially trapezoidal shape that narrows outwardly from an outer circumference of the stopper main body 62. By such a configuration, the distal end surface 66a does not impede the behavior of the stent 30 detaching outward in the radial direction of the stopper main body 62 or the inner sheath 10.

The upper surface 66b of the projection 66 is formed between the distal end surface 66a and the proximal end surface 66c, and may be configured to have a substantially trapezoidal shape that narrows toward the proximal end surface 66c in the longitudinal direction (axis) of the stopper main body 62 or the inner sheath 10.

The proximal end surface 66c is a recessed surface that includes a recess extending into a body of the projection 66 toward the distal end surface 66a, for example as seen in a side view of the stent stopper 60. As shown in FIG. 5, the proximal end surface 66c includes two slope surfaces (665a and 665b in FIG. 8C), and may be formed by cutting into the distal side of the stopper main body 62 in the longitudinal direction of the inner sheath 10. The two slope surfaces are inclined in different angles toward the distal end surface 66a, thereby forming a recess extending into a body of the projection 66. As will be illustrated later in FIGS. 8A-8C, the proximal end surface may be a sloped surface, a curved surface, or any surface that includes a recess extending into a body of the projection 66 and that is suitable to recapture and also to re-release the stent 30. The wire of the stent 30, which is engaged with the proximal end surface 66c, may be partially accommodated by the recess of the proximal end surface 66c as shown in FIG. 8C.

With such a configuration, the stent 30 is restrained on the proximal end surface 66 c by engaging the proximal end surface 66c with the mesh at the proximal end 31 of the stent 30. As a result, the stent 30 is prevented from coming off from the outer diameter direction of the stopper 60 during the recapture operation.

The two side surface 66d of the projection 66 are each connected to the distal end surface 66a, the upper surface 66b, the proximal end surface 66c and the bottom surface 66e (or the stopper main body 62), respectively. Since the stent 30 includes wires, which have a rhombus mesh shape at the proximal end 31 of the stent 30, the two side surfaces 66d may be each configured to have a suitable shape that does not interfere with the mesh shape of the stent 30 and does not hinder the detachment of the stent 30 from the stopper 60. For example, the two side surfaces may be each recessed toward each other to increase a space for adjacent wires of the stent 30.

The structural configuration of the projection 66 is designed to offer maximum contacting areas with the wires of the stent 30 so as to grip the stent 30 during deployment, repositioning and/or recapturing of the stent 30.

The projection 66 may also be a hollow member. Projection 66 may be fully or partially elastic to adapt, such as by compression, to fit inbetween the inner and outer sheaths 10 and 20 or to better releasably grasp and/or hold the stent 30. The projection 66 may also be a coated projection, such as a metal or stainless steel coated with an elastic polymer. Further, the projection 66 may include a material, such as a polymeric material, having a degree of tackiness to better releasably grasp and/or hold the stent 30. The projection 66 may be made of the same material of the stopper main body 62 if they are integrally formed.

The stopper main body 62 of the stent stopper 60 is configured to be as thin as possible to minimize the size of the stent stopper 60.

The stent stopper 60 may be constructed from any biocompatible metal, desirably stainless steel, or polymeric material. The stent stopper 60 may be manufactured by any suitable technique, such as, but not limited to, electrical discharge machining, metal injection molding. Further, the stent stopper 60 may be made by a piece of metal using metal stamping technology. For example, stainless steel could be stamped to shape the projection 66. The stent main body 62 may be shaped around the inner sheath 10 and glued, crimped or swaged in place.

The invention is not limited to the shape of the stent stopper 60 as shown in FIG. 4, and other low profile stent stopper configurations may be used. As will be described later, the stent stopper 60 may include a pair of opposed projections (in FIG. 13B) extending radially outward from the circular stopper main body 62. The stent stopper 60 may include three projections (in FIG. 13C) that are evenly disposed on the circular stopper main body 62. The stent stopper 60 may include four projections (in FIG. 13D) that are evenly disposed on the circular stopper main body 62. Other numbers of projections can also be used.

Moreover, the invention is not limited to radially outwardly extending projections 66 as depicted in FIG. 4, and any suitable configuration for the low profile radially outwardly extending projections may be applicable to the present invention.

FIGS. 6A-6B are planar top views schematically illustrating some exemplary configurations of the upper surface 66b.

As shown in FIG. 6A, the upper surface 66a may be configured to have a trapezoid shape 660. Such a configuration may be shaped to be conformal to the reduced diameter arc shape of the stent mesh. By this configuration, the contact area between the wires of the stretched stent mesh of the stent 30 and the side surfaces 66d of the stent stopper 60 increases when the stent 30 is loaded on and restrained by the stent stopper 60. As a result, a strong and stable restraint force in the longitudinal direction of the stopper main body 62 or the inner sheath 10 is obtained and more stable restraint of the stent 30 by the stent stopper 60 becomes possible.

As shown in FIG. 6B, the upper surface 66a may be configured to have a substantially half-elliptical (substantially half-rhombic) shape 661 having a narrower arc toward the proximal side of the inner sheath 10. Such a configuration may be shaped to be conformal to the reduced diameter arc shape of the stent mesh of the stent 30. By this configuration, the contact area between the wires of the stretched stent mesh of the stent 30 and the side surfaces 66d of the stent stopper 60 increases when the stent 30 is loaded on and restrained by the stent stopper 60. As a result, a strong and stable restraint force in the longitudinal direction of the stopper main body 62 or the inner sheath 10 is obtained and more stable restraint of the stent 30 by the stent stopper 60 becomes possible.

FIG. 7 is a schematic view illustrating the structural configuration of the upper surface 66b. As shown in FIG. 7, the structure of the upper surface 66b is configured to increase the contact area by matching the shape of the upper surface 66b of the projection 66 with the shape of the stretched stent mesh that is constrained by the projection 66, such as by hooking. An angle α (>0°) is defined by the projection of two side lines 666 and 667 of the upper surface 66b intersecting in the longitudinal direction. A length W1 is a width of the proximal end of the upper surface 66b (which is a distance between the two side lines 666 and 667 at the proximal end of the upper surface 66b). An angle β (>0°) is defined by two tangents lines L1 and L2 drawn to the two curved wire portions 301 and 302 of the stent 30 and intersecting in the longitudinal direction. A length W2 is a width between the two curved wire portions 301 and 302 at two points P1 and P2 at which the two curved wire portions 301 and 302 contact the proximal end of the upper surface 66b. In this exemplary embodiment, W1=W2, and it is acceptable that α=β or α<β.

Figure 8A:
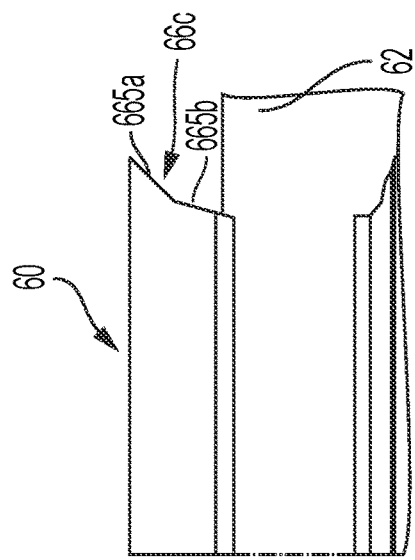
FIGS. 8A-8C are schematic side views illustrating different shapes of a proximal end surface of a projection of a stent stopper and various embodiments of a recess extending into a body of the projection according to various embodiment.
Figure 8B:
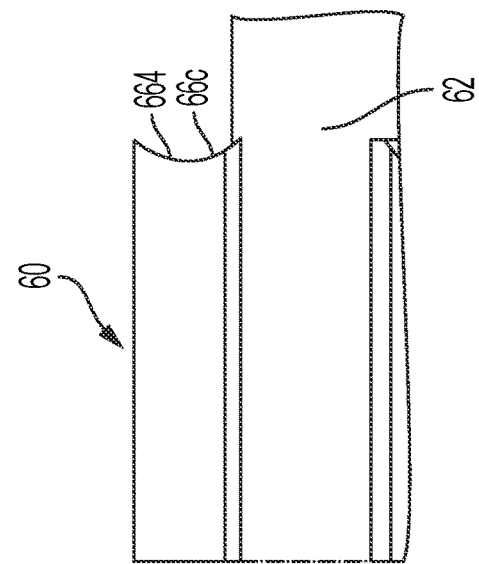
Figure 8C:
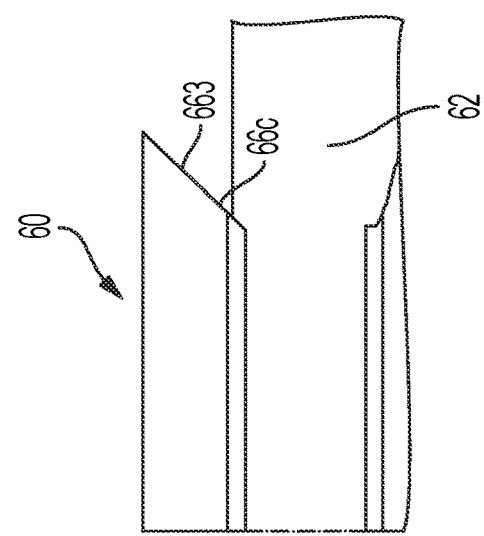

FIGS. 8A-8C are schematic side views illustrating different shapes of the recess of the proximal end surface 66c according to different exemplary embodiments. As shown in FIG. 8A, the proximal end surface 66c may include a slope 663 that is inclined toward the distal end surface 66a, thereby forming a recess extending toward the distal end surface 66a. Or the proximal end surface 66c may be configured to have a taper shape projected from the stopper main body 62. As shown in FIG. 8B, the proximal end surface 66c may be configured to have an arc shape 664 opening toward the proximal end surface 66c, thereby forming a recess extending toward the distal end surface 66a. As shown in FIG. 8C, the proximal end surface 66c may be configured to have multiple slopes including a first slope 665a and a second slope 665b, thereby forming a recess extending toward the distal end surface 66a. The first slope 665a and the second slope 665b are inclined at different angles, and thus form a two-step configuration. Or, the proximal end surface 66c may be configured to have multi-step taper shapes including a first taper shape and a second taper shape projected from the stopper main body 62.

Figure 9C:
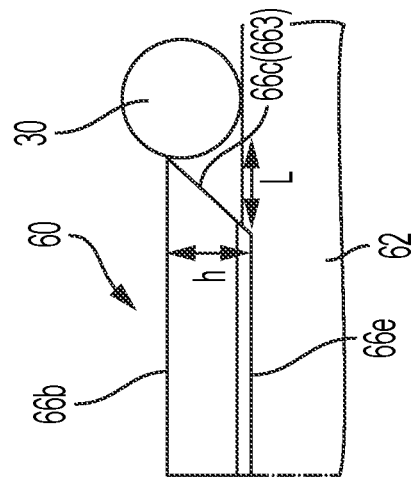
FIGS. 9A-9C are schematic views illustrating the structural relationship between the proximal end surface of the projection of the stent stopper, the recess, and the stent according to various embodiment.
Figure 9B:
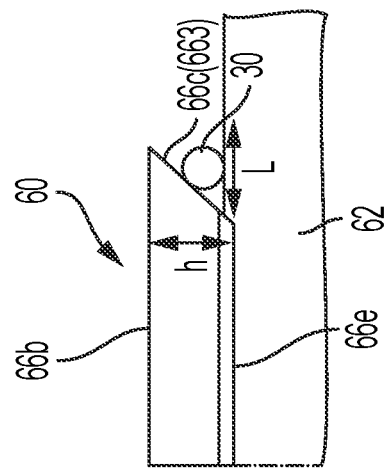
Figure 9A:
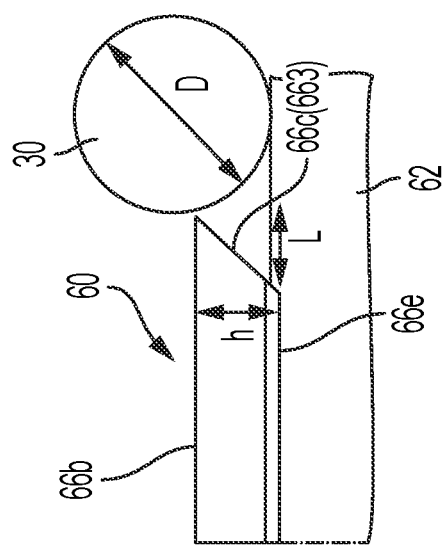

FIGS. 9A-9C are schematic views illustrating the structural relationship between the proximal end surface 66a and the stent 30. The stent 30 is represented by a circle indicative of a cross-section of the mesh wire along the edge of the stent 30. The stent 30 is restrained in the longitudinal direction of the inner sheath 10 or the stopper main body 62. The proximal end surface 66a serves as a receiving part at which the stent 30 is restrained. The functioning of the receiving part is enhanced in embodiments where a recess is included in the proximal end surface 66a. The receiving part has a height "h", which is measured as a distance between the stopper main body 62 and the upper surface 66b. The wire of the stent 30 has a diameter "D". FIG. 9A shows that the height "h" of the receiving part (the proximal end surface 66a) is smaller than the radius (r, which is equal to half the diameter "D") of the wire as shown. In this situation (i.e., h<r), when the stent 30 receives a load in the longitudinal direction, the stent 30 cannot be restrained by the proximal end surface 66*c* of the stent stopper 60, and thus there is no effect of restraining the stent 30 in the longitudinal direction. Therefore, the height "h" of the proximal end surface 66*c* should be larger than the radius of the stent wire as shown in FIG. 9C.

FIG. 9B shows a situation in which the height "h" of the receiving part (the proximal end surface 66*a*) is larger than the diameter "D" of the wire of the stent 30. In this situation, the stent 30 cannot detach (or release) from the proximal end surface 66*c*.

Figure 12:
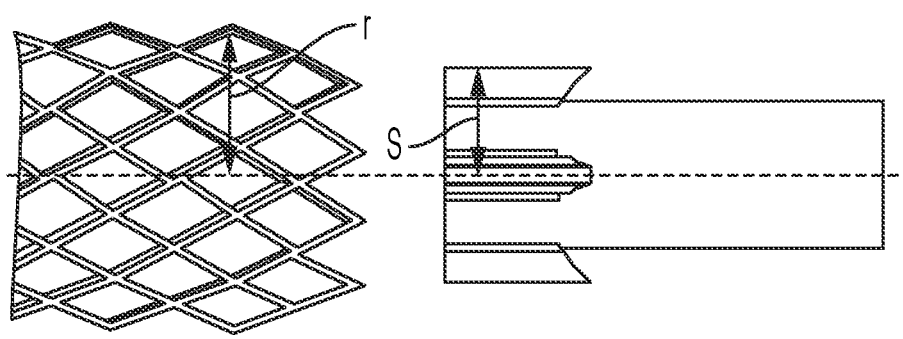
FIG. 12 is a side view schematically illustrating a structure relationship between a stent stopper and a fully expanded stent according to one exemplary embodiment.

In order for the stent 30 to smoothly detach/release from the proximal end surface 66*c* of the stent stopper 60, as shown in FIG. 12, the sum "s" of the height "h" of the proximal end surface 66*c* and a radius of an outer diameter surface of the stopper main body 62 must be smaller than an inner radius "r" of the fully expanded stent 30. By this configuration, the stent stopper 60 can restrain the stent 30 in the longitudinal direction, but also does not inhibit the detachment or the release of the stent 30.

Figure 10B:
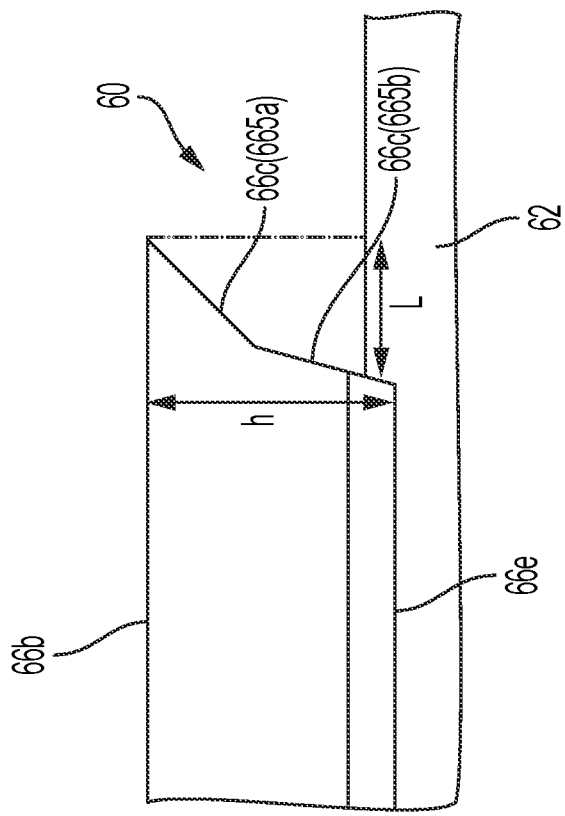
FIGS. 10A and 10B are schematic views illustrating the structural configuration of the proximal end surface of a projection and different embodiments of a recess extending into a body of the projection and the stent.
Figure 10A:
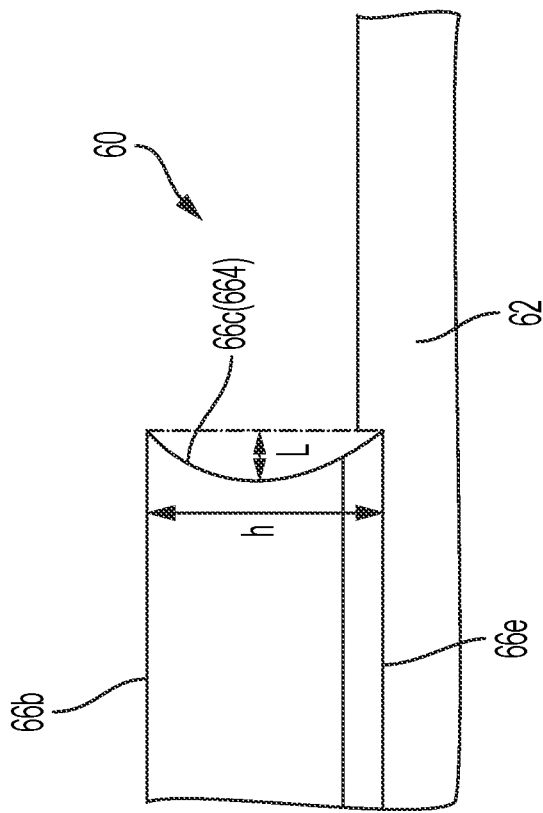

FIGS. 10A and 10B are schematic views illustrating the structural relationship between the proximal end surface 66*c* (664 and 665*a*/665*b*) and the stent 30. The proximal end surface 66*c* also has an axial length "L". As shown in FIGS. 9A-9C, the axial length "L" of the proximal end surface 66*c* (663) is defined as an axial distance between the proximal end of the upper surface 66*b* and the proximal end of a bottom surface 66*e*. As shown in FIG. 10A, the axial length "L" of the proximal end surface 66*c* (664) is the depth (or sagitta) of the arc shape of the proximal end surface 66*a* (664). As shown in FIG. 10B, the axial length "L" of the proximal end surface 66*c* (665*a* and 665*b*) is defined as an axial distance between the proximal end of the upper surface 66*b* and the proximal end of the bottom surface 66*e* (or the point where the proximal end surface 66*c* meets the main body 62).

In the exemplary embodiment, the axial length "L" of the receiving portion (the proximal end surface 66*c*) must be smaller than or equal to the radius of the wire of the stent 30 so that the proximal end surface 66*c* does not inhibit the detachment of the stent 30 from the stent stopper 60. If the axial length "L" of the receiving portion (the proximal end surface 664) is larger than the radius of the wire of the stent 30, the stent 30 cannot be smoothly self-expanded and released from the stent stopper 60.

In short, the height of the proximal end surface 66*c* of the stent stopper 60 is larger than the radius of the wire of the stent 30, and the sum of the height "h" of the proximal end surface 66*c* and the radius of the outer diameter surface of the stopper main body 62 is smaller than the inner radius of the fully expanded stent 30. Further, the axial length "L" of the proximal end surface 66*c* is smaller than or equal to the radius of the wire of the stent 30.

Figure 11:
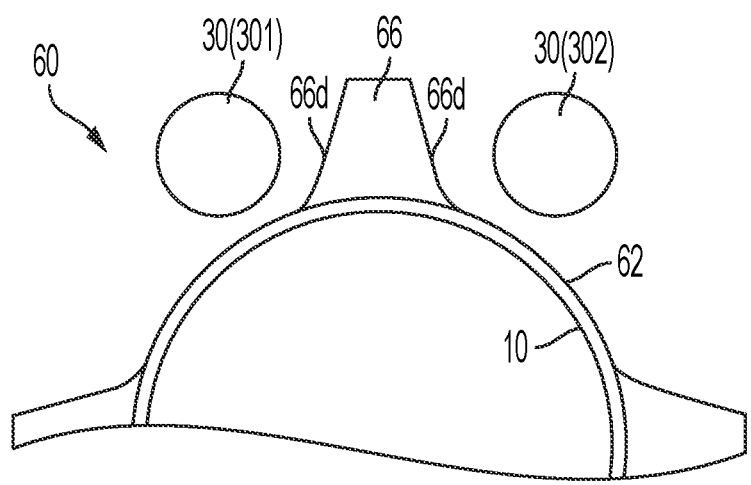
FIG. 11 is a cross-sectional view schematically illustrating a structure of the stent stopper according to one exemplary embodiment.

FIG. 11 is a cross-sectional view schematically illustrating a structure of the stent stopper 60 according to an exemplary embodiment. As shown in FIG. 11, the stopper main body 62 of the stent stopper 60 is disposed around the inner sheath 10. The stent 30 is restrained by the projection 66 of the stent stopper 60 such that two wire portions 301 and 302 sandwich the two side surfaces 66*d* of the projection 66.

FIG. 12 is a side view schematically illustrating a further structure relationship between the stent stopper 60 and a fully expanded stent 30 according to one exemplary embodiment. As also described above, the sum "s" of the height "h" of the proximal end surface 66*c* and the radius of the outer diameter surface of the stopper main body 62 must be smaller than an inner radius "r" of the fully expanded stent 30. By this configuration, the stent stopper 60 can be inserted into the interior opening of the expanded stent and the expanded stent can be positioned longitudinally past the projection 66 so as to securely recapture the stent 30. At the same time, the stent stopper 60 does not inhibit the detachment or the release of the stent 30.

FIGS. 13A-13D show examples of the stent stopper 60 according to additional embodiments. As shown in FIG. 13A, the stent stopper 60 may have only one projection 66 formed on the stopper main body 62. As shown in FIG. 13B, the stent stopper 60 may have two projections 66 symmetrically formed on the stopper main body 62. As shown in FIG. 13C, the stent stopper 60 may have three projections 66 that are evenly spaced around the stopper main body 62. As shown in FIG. 13D, the stent stopper 60 may have four projections 66 that are evenly spaced around the stopper main body 62. The invention is not limited to the structures illustrated in FIGS. 13A-13D. The stent stopper 60 of the invention may have more than four projections 66, which may be either symmetrically arranged with respect to one or another or be evenly spaced around the stopper main body 62 or be evenly spaced in groups around the stopper main body 62 or be unevenly spaced around the stopper main body 62.

Figure 14C:
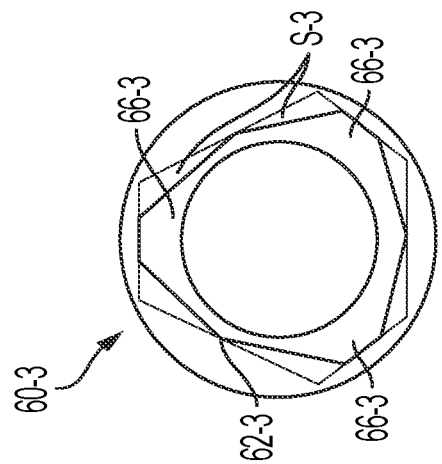
FIGS. 14A-14C are schematic views illustrating structural modifications of the stent stopper according to additional embodiments.
Figure 14B:
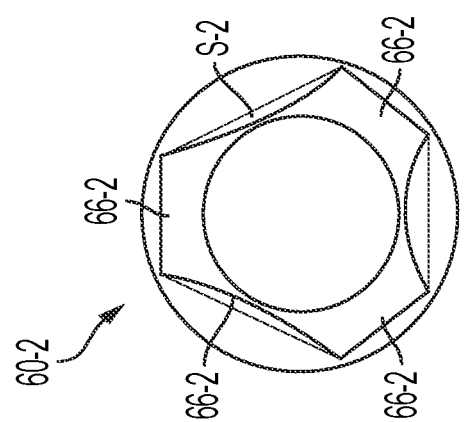
Figure 14A:
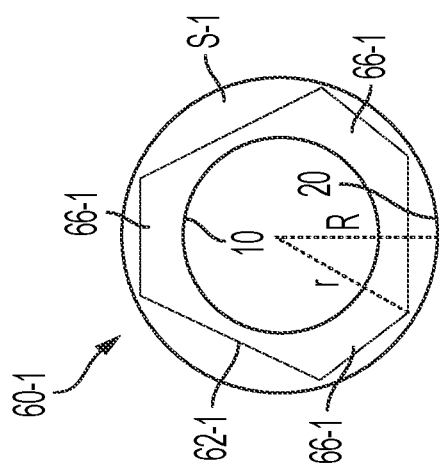

FIGS. 14A-14C are the schematic views illustrating structural modifications of a stent stopper according to additional embodiments. Specifically, the stent stopper may be modified to include a projection that has a gradient outwardly in the radial direction of the stopper main body as long as it does not hinder the detachment of the stent. For example, each vertex of the polygonal shape with a gradient toward the outside in the radial direction.

FIG. 14A shows a cross-sectional shape of a modified stent stopper 60-1 in which the vertices of an equilateral triangle are truncated, and the wires of the stent 30 may be constrained at each truncated vertex. In this exemplary modification, the stent stopper 60-1 is configured not to hinder the movement of the outer sheath 20 to release and recapture the stent 30 in the delivery system 100. In particular, the size of the stent stopper 60-1 is predetermined so as to reduce frictional force generated between the stopper 60-1 and the outer sheath 20 and to facilitate the operation of release/recapture of the stent 30 when sliding the outer sheath 20. Therefore, a length from the center of the stopper 60-1 to each of the furthest vertices must be smaller than an inner radius of the outer sheath 20. As shown in FIG. 14A, if the inner radius of the outer sheath 20 is R, and the length from the stopper center to each truncated vertex is r, there is a relationship of r<R.

With such a configuration, when the stent 30 is constrained by the stent stopper 60-1, the wires of the stent 30 that are not caught by the projection 66-1 reside in a space S-1 between the outer sheath 20 and the stopper 60-1. The volume of the space S-1 is set to be sufficient compared to the volume of the wires of the stent 30 so as to accommodate those wires that are not caught by the projection 66-1. Thus, the frictional force between the wires of the stent 30 and the inner side of the outer sheath 20 can be reduced, thereby facilitating the release/recapture operation of the delivery system.

FIG. 14B illustrates another exemplary modified stent stopper 60-2 that aims to further improve the release/recapture operability of the delivery system 100 in addition to the effect of increasing the constraining force in the longitudinal direction of the stent 30 by further increasing a space between the outer sheath 20 and the stopper 60-2.

Specifically, the straight side in the cross-sectional shape of the stopper 60-1 in FIG. 14A is formed into a concave curve at the center of the stopper main body 62-2 to widen the space between the outer sheath 20 and the stopper 60-2. The stopper 60-1 shown in FIG. 14B is merely used to compare with the stopper 60-2 of FIG. 14B. As shown in FIG. 14B, a space S-2 is formed between the outer sheath 20 and the stopper 60-2, and the wires of the stent 30 that are not caught by the projection 66-2 reside in a space S-2. Compared to the space S-1, the space S-2 is extended further inwardly in a radial direction, and therefore is larger than the space S-1 of FIG. 14A. Thus, the modified stopper 60-2 can provide more space to accommodate the wires of the stent 30.

FIG. 14C shows another modified stopper 60-3 that is also configured to further increase a space between the stent stopper and the outer sheath so as to achieve a better effect than the modification in FIG. 14A. Different from FIG. 14B, the modified stopper 60-3 in FIG. 14C is configured to have a convex in the center of the main body 62-3. The stopper 60-1 shown in FIG. 14C is merely used to compare with the stopper 60-3 of FIG. 14C. As shown in FIG. 14C, a space S-3 is formed between the outer sheath 20 and the stopper 60-3c, and the wires of the stent 30 that are not caught by the projection 66-3 reside in a space S-2. As the portions other than the center of the main body 62-3 are extended inwardly in the radial direction to generate more space for the wires of the stent 30, the space S-3 is larger than the space S-1 of FIG. 14A. As a result, the modified stopper 60c can provide more space to accommodate the wires of the stent 30.

Figure 15B:
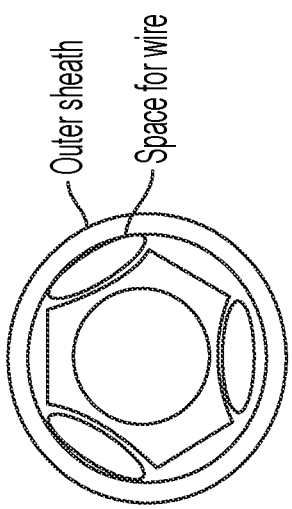
FIGS. 15A and 15B are schematic views illustrating the stent combined with the respective embodiments of FIGS. 14B and 14C.
Figure 15A:
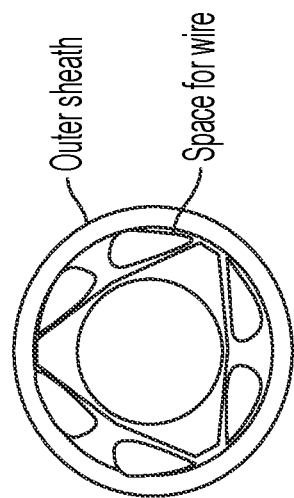

FIGS. 15A and 15B are schematic views illustrating the stent 30 combined with the respective modifications of FIGS. 14B and 14C. As shown in FIGS. 15A and 15B, the modifications of FIGS. 14B and 14C can increase space between the inner sheath 10 and the outer sheath 20 so that more space is provided to accommodate the wires of the stent 30.

While the embodiments of the present invention have been described and illustrated above, it should be appreciated by those skilled in the art that these are exemplary of the invention and are not to be considered as limiting. Additions, omissions, substitutions, and other modifications can be made without departing from the spirit and scope of the present invention. Accordingly, the invention is not to be considered as being limited by the foregoing description, and is only limited by the scope of the appended claims.

What is claimed is:

1. A stent delivery device for delivering a self-expanding stent, comprising:
   an inner sheath including a proximal end portion and a distal end portion;
   a stent stopper including a main body that is circumferentially disposed over at least a portion of the inner sheath at the proximal end portion, and at least one projection extending radially outward from the main body for releasably engaging a portion of the self-expanding stent; and
   an outer sheath slidably disposed over the inner sheath and the stent stopper,
   wherein the at least one projection includes a radially upper surface extending between a distal end surface and a proximal end surface,
   wherein the upper surface has a substantially trapezoid shape that continuously narrows from a first base at the distal end surface to a second base at the proximal end surface, and
   wherein the proximal end surface includes a recess extending into a body of the at least one projection toward the distal end surface.

2. The stent delivery device according to claim 1, wherein the distal end surface of the at least one projection has a substantially trapezoidal shape that narrows outwardly from an outer circumference of the stopper main body.

3. The stent delivery device according to claim 1, wherein the upper surface has a trapezoidal shape.

4. The stent delivery device according to claim 1, wherein the at least one projection includes two side surfaces that are configured to be recessed toward each other.

5. The stent delivery device according to claim 1, wherein the proximal end surface includes a slope that extends toward the distal end surface.

6. The stent delivery device according to claim 1, wherein the proximal end surface includes multiple slopes, which includes at least a first slope and a second slope that are inclined in different angles toward the distal end surface.

7. The stent delivery device according to claim 1, wherein the proximal end surface includes an arc surface that is curved toward the distal end surface.

8. The stent delivery device according to claim 1, wherein the stent stopper includes two opposed projections.

9. The stent delivery device according to claim 8, wherein the two projections are circumferentially disposed on the stopper main body to be symmetrical to each other.

10. The stent delivery device according to claim 1, wherein the stent stopper includes a plurality of projections, which are evenly disposed around an outer circumference of the stopper main body.

11. The stent delivery device according to claim 1, wherein the proximal end surface is configured to engage a mesh shaped wire of the self-expanding stent,
   wherein the proximal end surface has a height from the stopper main body, and wherein the height is larger than a radius of the wire.

12. The stent delivery device according to claim 11, wherein
   the proximal end surface has an axial length, and
   wherein the axial length is smaller than the radius of the wire.

13. The stent delivery device according to claim 12, wherein the self-expanding stent includes an inner radius when the stent is fully expanded, and the stopper main body includes an outer radius, and
   wherein a sum of the height of the proximal end surface and the outer radius of the main body is configured to be smaller than the inner radius of the fully expanded stent.

14. The stent delivery device according to claim 1, wherein the substantially trapezoid shape of the upper surface is configured to increase a contact area with a stretched stent mesh constrained by the at least one projection.

15. The stent delivery device according to claim 1, wherein a portion of the proximal end surface located at a distance spaced apart from an intersection point of the proximal end surface and the second base of the upper surface is, in the longitudinal direction of the inner sheath, distal from the intersection point and, in a radial direction of the inner sheath, inward from the intersection point.

16. A stent delivery device for delivering a self-expanding stent, comprising:
   an inner sheath including a proximal end portion and a distal end portion;

a stent stopper including a main body that is circumferentially disposed over at least a portion of the inner sheath at the proximal end portion, and at least one projection extending radially outward from the main body for releasably engaging a portion of the self-expanding stent; and an outer sheath slidably disposed over the inner sheath and the stent stopper, wherein the at least one projection includes a distal end surface, a proximal end surface, and an upper surface that is formed between the distal end surface and the proximal end surface; and wherein the upper surface has a substantially trapezoidal shape that continuously narrows toward the proximal end surface in a longitudinal direction of the inner sheath over an entire longitudinal length of the upper surface.

17. The stent delivery device according to claim 16, wherein the stent stopper includes two opposed projections.

18. The stent delivery device according to claim 17, wherein the two projections are circumferentially disposed on the stopper main body to be symmetrical to each other.

19. The stent delivery device according to claim 16, wherein the stent stopper includes a plurality of projections, which are evenly disposed around an outer circumference of the stopper main body.

20. The stent delivery device according to claim 16, wherein the proximal end surface is configured to engage a mesh shaped wire of the self-expanding stent, wherein the proximal end surface has a height from the stopper main body, and wherein the height is larger than a radius of the wire.

21. The stent delivery device according to claim 20, wherein the proximal end surface has an axial length, and wherein the axial length is smaller than the radius of the wire.

22. The stent delivery device according to claim 21, wherein the self-expanding stent includes an inner radius when the stent is fully expanded, and the stopper main body includes an outer radius, and wherein a sum of the height of the proximal end surface and the outer radius of the main body is configured to be smaller than the inner radius of the fully expanded stent.

* * * * *